(12) United States Patent
Lin et al.

(10) Patent No.: US 8,933,269 B2
(45) Date of Patent: Jan. 13, 2015

(54) ROSUVASTATIN CALCIUM INTERMEDIATE AND METHOD FOR PREPARING THE SAME

(75) Inventors: Wenqing Lin, Chongqing (CN); Hongjie Zheng, Chongqing (CN); Xiaobo Liu, Chongqing (CN)

(73) Assignee: Porton Fine Chemicals Ltd., Chongqing (CN)

( * ) Notice: Subject to any disclaimer, the term of this patent is extended or adjusted under 35 U.S.C. 154(b) by 74 days.

(21) Appl. No.: 13/587,913

(22) Filed: Aug. 16, 2012

(65) Prior Publication Data

US 2012/0310000 A1 Dec. 6, 2012

Related U.S. Application Data

(63) Continuation-in-part of application No. PCT/CN2010/075519, filed on Jul. 28, 2010.

(30) Foreign Application Priority Data

Apr. 5, 2010 (CN) .......................... 2010 1 0162885
May 21, 2010 (CN) .......................... 2010 1 0179187

(51) Int. Cl.
| | | |
|---|---|---|
| C07C 59/00 | (2006.01) | |
| C07F 9/535 | (2006.01) | |
| C07C 69/732 | (2006.01) | |
| C07C 29/36 | (2006.01) | |
| C07C 67/22 | (2006.01) | |
| C07C 67/29 | (2006.01) | |
| C07C 67/31 | (2006.01) | |
| C07C 67/313 | (2006.01) | |
| C07C 69/734 | (2006.01) | |
| C07C 69/78 | (2006.01) | |

(52) U.S. Cl.
CPC .............. *C07F 9/5352* (2013.01); *C07C 69/732* (2013.01); *C07C 29/36* (2013.01); *C07C 67/22* (2013.01); *C07C 67/29* (2013.01); *C07C 67/31* (2013.01); *C07C 67/313* (2013.01); *C07C 69/734* (2013.01); *C07C 69/78* (2013.01)
USPC ....................................................... 562/579

(58) Field of Classification Search
None
See application file for complete search history.

(56) References Cited

U.S. PATENT DOCUMENTS 5,260,440 A    11/1993   Hirai et al.

FOREIGN PATENT DOCUMENTS

| WO | 2006/091771 A2 | 8/2006 |
| WO | 2006/091771 A3 | 8/2006 |
| WO | 2006091771 | * 8/2006 |

OTHER PUBLICATIONS

Database Caplus Chemical Abstracts Service, Columbus, Ohio, US; Database Accession No. 1988:529545, Abstract of Sun et al., Carbohydrate Research (1987), 171, 35-47.*
Database Caplus Chemical Abstracts Service, Columbus, Ohio, US; Database Accession No. 1991:509154, Abstract of Gordon et al., Bioorganic & Medicinal Chemistry Letters (1991), 1(1), 61-4.*
Vatèle, Synlett, 2006, 2055-2058.*
E.M.Gordon et al, Synthesis of Substrate-based Inhibitors of HMG CoA Reductase, Bioorganic & Medicinal Chemistry Letters, 1991, pp. 61-64, vol. 1, No. 1, Pergamon Press plc, Great Britain.
Frank Bennett et al, Methyl(3R)-3-hydroxyhex-5-enoate as a Precursor to Chiral Mevinic Acid Analogues, J. Chem. Soc. Perkin Trans., 1991, pp. 133-140, vol. 1, Great Britain.

* cited by examiner

*Primary Examiner* — Karl J Puttlitz
(74) *Attorney, Agent, or Firm* — Matthias Scholl P.C.; Matthias Scholl

(57) ABSTRACT

A method for preparing a rosuvastatin calcium intermediate, including a) contacting a halogenated ethene with magnesium metal to obtain a halogenated ethene Grignard reagent, and carrying out a Grignard reaction between the halogenated ethene Grignard reagent and R-epichlorohydrin; b) adding sodium cyanide for carrying out a nucleophilic substitution reaction; c) adding alcohol for carrying out an alcoholysis reaction; d) adding a basic solvent for carrying out protection of a first hydroxyl group; e) selectively oxidizing a second hydroxyl group; and f) adding triphenylphosphine in alkaline condition for carrying out a Wittig reaction.

8 Claims, No Drawings

ROSUVASTATIN CALCIUM INTERMEDIATE AND METHOD FOR PREPARING THE SAME

CROSS-REFERENCE TO RELATED APPLICATIONS

This application is a continuation-in-part of International Patent Application No. PCT/CN2010/075519 with an international filing date of Jul. 28, 2010, designating the United States, now pending, and further claims priority benefits to Chinese Patent Application No. 201010162885.7 filed Apr. 5, 2010, and to Chinese Patent Application No. 201010179187.8 filed May 21, 2010. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

1. Field of the Invention

This invention relates to a medicament intermediate and method for preparing the same, and more particularly to a rosuvastatin calcium intermediate and method for preparing the same.

2. Description of the Related Art

Rosuvastatin calcium, with chemical name of (+)-(3R,5S)-7-[4-(4-fluorophenyl)-6-isopropyl-2-(N-methyl-N-mesyl amino)pyrimidine-5-yl]-3,5-dihydroxyl-6(E)-heptenoic acid calcium (2:1), is used for auxiliary treatment of patients with primary hypercholesterolemia (IIa type, including heterozygous familial hypercholesterolemia) or combined hyperlipidemia (IIb type) when diet or exercise therapy is not ideal. Rosuvastatin calcium can lower rising LDL-cholesterol, total cholesterol, triglyceride, and ApoB, and increase HDL-cholesterol. Rosuvastatin calcium also applies to the patients with homozygous familial hypercholesterolemia, and can be used alone or used in combination with a dieting or other blood-fat depressing methods (e.g. LDL apheresis). Because of its advantages of high efficiency, low toxicity, and small side effect, rosuvastatin calcium is popular and has a broad application prospect. Its chemical structural formula is as follows:

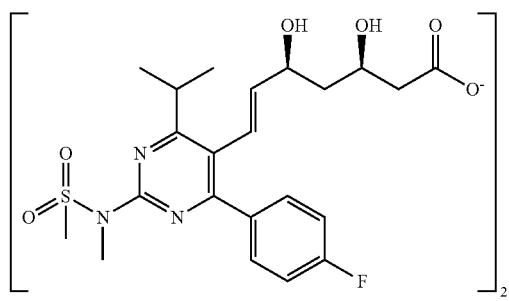

Methyl (3R)-3-(tert-butyldimethylsilyloxy)-5-oxo-6-triphenylphosphoranylidene hexanoate described in the invention is an important intermediate for preparing rosuvastatin calcium.

A typical method for preparing methyl (3R)-3-(tert-butyldimethylsilyloxy)-5-oxo-6-triphenylphosphoranylidene hexanoate by taking (3R)-3-(tent-butyldimethylsilyl)oxypentanedioate-1-methyl monoester as a raw material is described as follows:

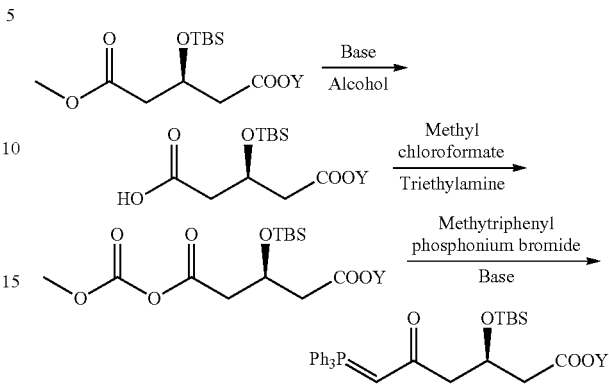

wherein, Y represents a carboxyl protecting group, TBS represents tert-butyldimethylsilyl, and Ph represents phenyl. In the method, the carboxyl protecting group Y must be a large group, so as to enhance the stability of the protected ester group and improve the selectivity of monomethyl ester hydrolysis in the first step reaction. If the carboxyl protecting group Y is a small group, for example, methyl, the difficulty in hydrolysis of monomethyl ester will be increased greatly, and the yield of the monomethyl ester hydrolysate is low and even fails to obtain. Therefore, the method is high in preparation cost and not suitable for large-scale industrial production.

Another conventional method for preparing methyl (3R)-3-(tert-butyldimethylsilyloxy)-5-oxo-6-triphenylphosphoranylidene hexanoate by taking an acid anhydride compound as a raw material is given below:

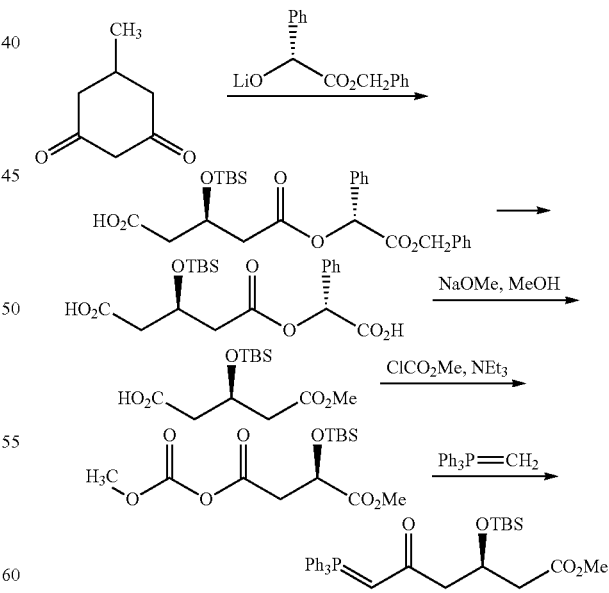

In the method, the used raw material acid anhydride compound is high in price, the yield of the product in the first step reaction is low, and the problem of high preparation cost also exists, therefore, the method is not suitable for large-scale industrial production.

SUMMARY OF THE INVENTION

In view of the above-described problems, it is one objective of the invention to provide a method for preparing a rosuvastatin calcium intermediate suitable for industrial production. The method is simple and easy to control, high in yield, good in purity, and low in cost.

To achieve the above objective, in accordance with one embodiment of the invention, there is provided a method for preparing a rosuvastatin calcium intermediate represented by formula I,

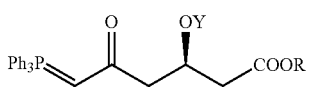

the method comprising contacting a compound represented by formula V

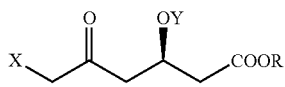

with triphenylphosphine in alkaline condition for carrying out a Wittig reaction; wherein R represents alkyl, Y represents a hydroxyl protecting group, and X represents a halogen atom.

In a class of this embodiment, R represents C1-C3 alkyl, Y represents tert-butyldimethylsilyl, benzyl, or benzoyl, and X is chlorine, bromine, or iodine.

In a class of this embodiment, the alkaline condition is provided by adding an alkali metal oxide, an alkaline-earth metal oxide, a hydroxide, a carbonate, a bicarbonate, or a mixture thereof to a reaction liquid, particularly, potassium carbonate, calcium carbonate, potassium bicarbonate, calcium bicarbonate, or a mixture thereof.

In a class of this embodiment, the compound represented by formula V is prepared as follows: in the presence of a nitroxyl radical, a selective oxidant, and a phase-transfer catalyst, selectively oxidizing a hydroxyl of a compound represented by formula IV

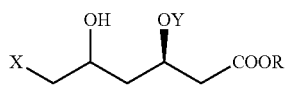

in a solvent A.

In a class of this embodiment, the solvent A is selected from the group consisting of methylene chloride, chloroform, carbon tetrachloride, ethyl acetate, butyl acetate, toluene, benzol, acetonitrile, acetone, butanone, n-hexane, cyclohexane, n-heptane, DMF, DMA, DMSO, a mixture thereof, and an aqueous solution thereof.

In a class of this embodiment, the nitroxyl radical is 2,2,6,6-tetramethylpiperidine-N-oxide.

In a class of this embodiment, the selective oxidant is sodium hypochlorite or sodium chlorite.

In a class of this embodiment, the phase-transfer catalyst is benzyltriethylammonium chloride, tetrabutyl ammonium bromide, tetrabutylammonium chloride, tetrabutyl ammonium hydrogen sulfate, methyltrioctylammonium chloride, or hexadecyltrimethylammonium chloride.

In a class of this embodiment, the compound represented by formula IV is prepared as follows: contacting a compound represented by formula III

with a halogenated reagent in a solvent B for a helogenation reaction.

In a class of this embodiment, the solvent B is selected from the group consisting of methylene chloride, chloroform, carbon tetrachloride, ethyl acetate, butyl acetate, toluene, benzol, acetonitrile, acetone, butanone, methanol, ethanol, isopropyl alcohol, n-hexane, cyclohexane, n-heptane, DMF, DMA, DMSO, a mixture thereof, and an aqueous solution thereof.

In a class of this embodiment, a temperature for the halogenation reaction is between −10 and 50° C.

In a class of this embodiment, a method for preparing the compound represented by formula III comprises the following steps:

a). contacting halogenated ethene with magnesium metal to obtain a halogenated ethene Grignard reagent, and carrying out a Grignard reaction between the halogenated ethene Grignard reagent and R-epichlorohydrin in the presence of a catalyst to obtain a (2R)-1-halogeno-2-hydroxyl-4-pentenyl compound;

b). carrying out a nucleophilic substitution reaction between the (2R)-1-halogeno-2-hydroxyl-4-pentenyl compound and sodium cyanide to obtain a (2R)-1-cyano-2-hydroxyl-4-pentenyl compound;

c). carrying out an alcoholysis reaction between the (2R)-1-cyano-2-hydroxyl-4-pentenyl compound and alcohol under the action of acid catalysis to obtain a compound represented by formula II;

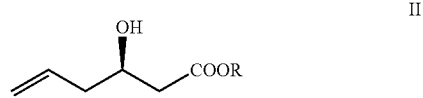

and d). performing hydroxyl protection to the compound represented by formula II in a basic solvent to obtain the compound represented by formula III.

In a class of this embodiment, the catalyst in step a) is cuprous chloride, cuprous iodide, and cuprous cyanide, and a mol ratio between the catalyst and R-epichlorohydrin is 0.10-0.15:1.

In a class of this embodiment, the basic solvent in step d) is a mixture of imidazole and an organic solvent.

In a class of this embodiment, a mol ratio between the imidazole and the compound represented by formula II is 1.5-2.5:1.

The invention provides a compound represented by formula V,

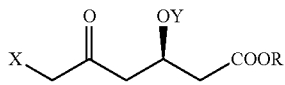

wherein:
X represents a halogen atom;
Y represents a hydroxyl protecting group; and
R represents an alkyl.

In a class of this embodiment, X is Br, Y is TBS, and R is methyl, there comes a compound represented formula VII

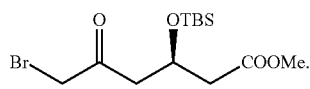

The invention further provides a compound represented by formula IV,

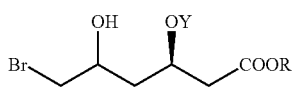

wherein:
X represents a halogen atom;
Y represents a hydroxyl protecting group; and
R represents an alkyl.

In a class of this embodiment, X is Br, Y is TBS, and R is methyl, there comes a compound represented formula VI

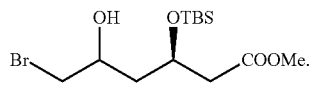

Advantages of the invention are summarized below: the rosuvastatin calcium intermediate (i.e., the compound represented by formula I) of the invention is prepared by a synthetic method totally different from the prior art. The method has the advantages of simple condition, no high temperature and high pressure reaction, easily purchased raw materials, catalysts, and oxidants, stable process, high yield of the product, no lots of three wastes produced, and small pollution to the environment, and thus is suitable for large-scale industrial production.

In the preparation process, two new compounds represented by formulas IV and V are also obtained, which are important intermediates for preparation of the compound represented by formula I.

DETAILED DESCRIPTION OF THE EMBODIMENTS

For further illustrating the invention, experiments detailing a rosuvastatin calcium intermediate and method for preparing the same are described below. It should be noted that the following examples are intended to describe and not to limit the invention

Example 1

Preparation of a compound represented by formula I-1,

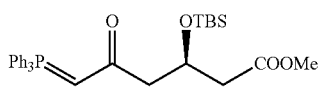

which is originated from formula I in which R is Me, and Y is TBS.

a. Carrying Out Reaction Between Chloroethylene and Magnesium Metal to Obtain a Chloroethylene Grignard Reagent, and then Carrying Out a Grignard Reaction Between the Chloroethylene Grignard Reagent and R-Epichlorohydrin to Obtain (2R)-1-chloro-2-hydroxyl-4-pentene

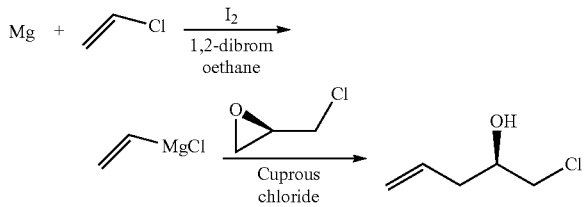

2700 mL of anhydrous tetrahydrofuran and 216 g of powdered magnesium are added to a reaction flask and evenly stirred, then 4.5 g of iodine and 100 g of 1,2-dibromoethane are added, and temperature is slowly raised to 60-64° C. and maintained for 3-4 h with stirring. Thereafter, chloroethylene is continuously introduced, and the solution is allowed to react for 10-11 h at the temperature of 60-64° C. Then temperature is dropped to 25-35° C., and the concentration of the chloroethylene Grignard reagent is measured to be 3.34 mol/L.

After the temperature of the reaction liquid is continued to be dropped to −35-25° C., 30 g of cuprous chloride is added, then 280 g of R-epichlorohydrin (the mol ratio between the cuprous chloride and R-epichlorohydrin is 0.10-0.15:1) is slowly dripped, temperature is kept at −35-25° C. in the dripping process, after 1-2 hours' dripping, the reaction liquid is transferred to 200 mL of saturated ammonium chloride solution precooled to 5-10° C., the pH value is adjusted to 3-4 with hydrochloric acid solution with concentration of 3 mol/L, extraction is carried out by three times with 150 mL of methyl tert-butyl ether, organic phases are combined, washing is carried out with 50 mL of saturated sodium bicarbonate solution and 50 mL saturated sodium chloride solution, solvents are evaporated at the temperature of 25-30° C. and under the vacuum degree of 250-350 Pa to obtain 306.9 g of viscous yellowish-brown liquid, i.e., (2R)-1-chloro-2-hydroxyl-4-pentene, its purity detected by high-performance liquid chromatography is 97.4%, and its yield is 81.9%.

b. Carrying Out a Nucleophilic Substitution Reaction Between (2R)-1-Chloro-2-hydroxyl-4-pentene and Sodium Cyanide to Obtain (2R)-1-cyano-2-hydroxyl-4-pentene

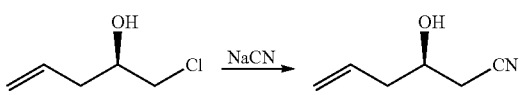

440 mL of pure water and 50 g of sodium cyanide are added to the reaction flask and stirred for dissolution, 82 g of (2R)-1-chloro-2-hydroxyl-4-pentene is dripped at the temperature of 30-35° C. Thereafter, the temperature is raised to 40-45° C. for reaction, and the reaction progress is monitored by thin-layer chromatography (The developing agent is a mixed liquor of petroleum ether-ethyl acetate (5:1 in volume ratio)) until the complete reaction of (2R)-1-cyano-2-chloro-4-pentene. The temperature of the reaction liquid is dropped to 30-35° C., extraction is carried out by three times with 600 mL of chloroform, organic phases are combined, washing is carried out with saturated sodium chloride solution, drying is carried out with 30 g of anhydrous sodium sulfate, solvents are evaporated at the temperature of 30-40° C. and under the vacuum degree of 250-350 Pa to obtain 66.6 g of brown liquid, i.e., (2R)-1-cyano-2-hydroxyl-4-pentene, its purity detected by gas chromatography is 99.7%, and its yield is 90.2%.

c. Carrying Out Alcoholysis Reaction Between the (2R)-1-cyano-2-hydroxyl-4-pentene and Methanol Under the Action of Dried Hydrogen Chloride Gas to Obtain a Compound Represented by Formula II-1

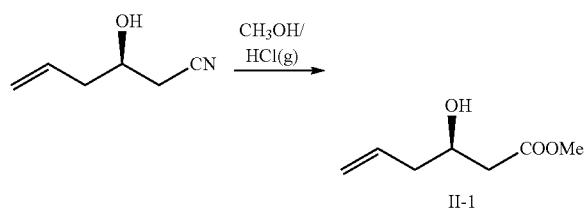

300 mL of absolute methanol and 62 g of (2R)-1-cyano-2-hydroxyl-4-pentene (GC: 99.7%) are added to the reaction flask to be evenly stirred, dried hydrogen chloride gas is introduced for reaction by stirring at the room temperature, the reaction progress is monitored by thin-layer chromatography (The developing agent is a mixed liquor of petroleum ether and ethyl acetate (1:1 in volume ratio)) until the complete reaction of (2R)-1-cyano-2-hydroxyl-4-pentene, a part of methanol in the reaction liquid is evaporated at the temperature of 35° C. and under the vacuum degree of 250-350 Pa, 400 mL of water is added for uniform mixing, extraction is carried out by three times with 600 g of chloroform, organic phases are combined, washing is carried out with 200 mL of saturated sodium bicarbonate solution, drying is carried out with 100 g of anhydrous sodium sulfate, solvents are evaporated at the temperature of 45° C. to obtain 70.9 g of brown liquid, i.e., the compound represented by formula II-1, its purity detected by HPLC (High-performance liquid chromatography) is 91.0%, and its yield is 80.5%.

d. Preparation of a Compound Represented by Formula III-1

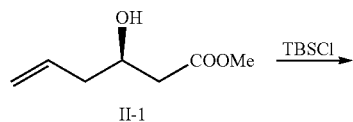

33.4 g of imidazole, 50 mL of methylene chloride, and 37 g of a compound represented by formula II-1 (HPLC: 91.0%, and the mol ratio between the imidazole and the compound represented by formula II-1 is 1.5-2.5:1) are added to the reaction flask for stirring to become clear, a mixed liquor of 46.4 g of TBSCl and 70 mL of methylene chloride is dripped, then reaction is carried out during stirring at the temperature of 25-30° C., the reaction progress is monitored by thin-layer chromatography (The developing agent is a mixed liquor of petroleum ether-ethyl acetate (3:1 in volume ratio)) until the complete reaction of the compound represented by formula II-1, then the reaction liquid is transferred to 100 mL of water, extraction is carried out by three times with 150 g of methylene chloride, organic phases are combined, washing is carried out with 100 mL of saturated sodium bicarbonate solution and 100 mL of saturated sodium chloride solution, solvents are evaporated at the temperature of 30-35° C. and under the vacuum degree of 250-350 Pa to obtain 63.1 g of light yellow liquid, i.e., the compound represented by formula III-1, its purity detected by gas chromatography is 88.1%, and its yield is 92.1%.

e. Preparation of a Compound Represented by Formula IV-1

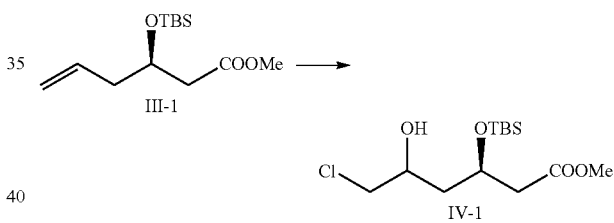

17.6 g of a compound represented by formula III-1 (GC: 88.1%) and 250 mL of acetone are added to a 1 L reaction flask, the temperature of the system is dropped to 0-15° C. after complete dissolution, 10.9 g of N-chlorosuccinimide is added in batches, then the system reacts with heat preservation at the temperature of 40-50° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 21.3 g of crude product of the compound represented by formula IV-1, its purity detected by GC (gas chromatography) is 86.6%, and its yield is 98.9%.

1H NMR (300 MHz, CDCl$_3$): δ4.31-4.35 (m, 1H), δ3.90-4.10 (m, 1H), δ3.66 (s, 3H), δ3.36-3.46 (m, 2H), δ2.54-2.59 (m, 2H), δ1.75-1.81 (m, 2H), δ0.86 (s, 9H), δ0.09 (s, 3H), δ0.07 (s, 3H)

f. Preparation of a Compound Represented by Formula V-1

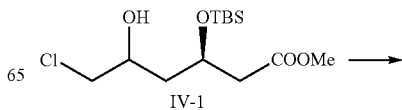

-continued

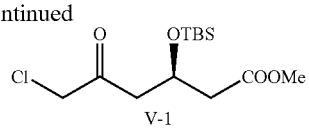

21.3 g of a compound represented by formula IV-1 (GC: 86.6%), 0.2 g of tetrabutylammonium bromide, 0.4 g of potassium bromide and 0.2 g of TEMPO are added to a 500 mL reaction flask, then 150 mL of n-hexane is added, 35 mL of sodium bicarbonate solution is added after the system is cooled to −10-10° C., 120 g of sodium hypochlorite is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 20.5 g light yellow liquid, i.e., the compound represented by formula V-1, its purity detected by GC (gas chromatography) is 70.0%, and its yield is 78.3%.

1H NMR (300 MHz, CDCl$_3$): δ4.52-4.60 (m, 1H), δ4.12 (s, 2H), δ3.65 (s, 3H), δ2.72-2.89 (m, 2H), δ2.44-2.58 (m, 2H), δ0.82 (s, 9H), δ0.06 (s, 3H), δ0.04 (s, 3H)

g. Preparation of a Compound Represented by Formula I-1

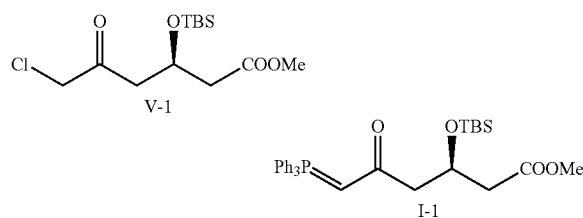

20.5 g of a compound represented by formula V-1 (GC: 70.0%), 26.0 g of triphenylphosphine, 18.2 g of potassium carbonate and 61.5 mL of DMF are added to the 500 mL reaction flask, and the system reacts at the temperature of 20-30° C. In the middle control of GC, 100 mL of water is added to the system for dissolution of solid after complete reaction of the compound represented by formula V-1, extraction is carried out by three times with 100 mL×3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-1, 50 g of ethyl acetate/petroleum ether (2:1) is added for crystallization, 7.9 g of a compound represented by formula I-1 is obtained after filtering and drying, its purity detected by HPLC (high-performance liquid chromatography) is 96.5%, its ee value is 99.7%, and its yield is 30.6%.

1H NMR (300 MHz, CDCl$_3$): δ7.46-7.70 (m, 15H), δ4.54-4.59 (m, 1H), δ3.67 (s, 3H), δ2.73-2.77 (m, 1H), δ2.59-2.63 (m, 1H), δ2.45-2.55 (m, 2H), δ0.83 (s, 9H), δ0.03-0.06 (m, 6H).

MS: m/z=535.5 [M+H]+

Example 2

Preparation of a compound represented by formula I-2,

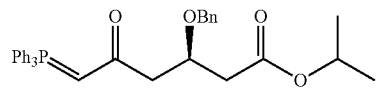

which is originated from formula I in which R is isopropyl, and Y is Bn.

The preparation steps a and b are the same as the steps a and b in example 1.

c. Carrying out Alcoholysis Reaction Between the (2R)-1-cyano-2-hydroxyl-4-pentene and Isopropyl Alcohol Under the Action of Dried Hydrogen Chloride Gas to Obtain a Compound Represented by Formula II-2

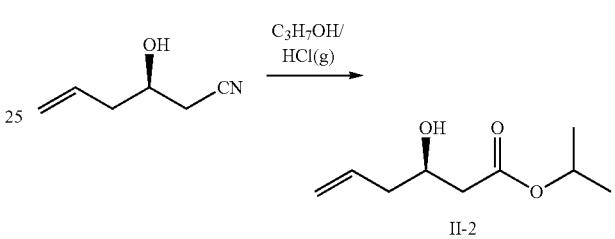

300 mL of anhydrous isopropyl alcohol and 62 g of (2R)-1-cyano-2-hydroxyl-4-pentene (GC: 99.4%) are added to the reaction flask to be evenly stirred, dried hydrogen chloride gas is introduced for reaction by stirring at the room temperature, the reaction progress is monitored by thin-layer chromatography (The developing agent is a mixed liquor of petroleum ether-ethyl acetate (1:1 in volume ratio)) until the complete reaction of (2R)-1-cyano-2-hydroxyl-4-pentene, about two-thirds of isopropyl alcohol in the reaction liquid is evaporated at the temperature of 35° C. and under the vacuum degree of 250-350 Pa, 400 mL of water is added for uniform mixing, extraction is carried out by three times with 600 g of chloroform, organic phases are combined, washing is carried out with 200 mL of saturated sodium bicarbonate solution, drying is carried out with 100 g of anhydrous sodium sulfate, solvents are evaporated at the temperature of 30-40° C. and under the vacuum degree of 250-350 Pa to obtain 84.7 g of brown liquid, i.e., the compound represented by formula II-2, its purity detected by HPLC (High-performance liquid chromatography) is 91.6%, and its yield is 81.3%.

d. Preparation of a Compound Represented by Formula III-2

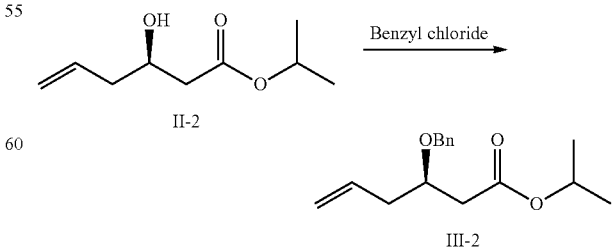

26.3 g of imidazole, 40 mL of methylene chloride and 35 g of a compound represented by formula II-2 (HPLC: 91.6%)

are added to the reaction flask for stirring to become clear, a mixed liquor of 31 g of benzyl chloride and 70 mL of methylene chloride is dripped, then reaction is carried out during stirring at the temperature of 25-30° C., the reaction progress is monitored by thin-layer chromatography (The developing agent is a mixed liquor of petroleum ether-ethyl acetate (3:1 in volume ratio)) until the complete reaction of the compound represented by formula II-2, then the reaction liquid is transferred to 100 mL of water, extraction is carried out by three times with 150 g of methylene chloride, organic phases are combined, washing is carried out with 100 mL of saturated sodium bicarbonate solution and 100 mL of saturated sodium chloride solution, solvents are evaporated at the temperature of 30-35° C. and under the vacuum degree of 250-350 Pa to obtain 52.3 g of light yellow liquid, i.e., the compound represented by formula III-2, its GC is 86.5%, and its yield is 92.6%.

e. Preparation of a Compound Represented by Formula IV-2

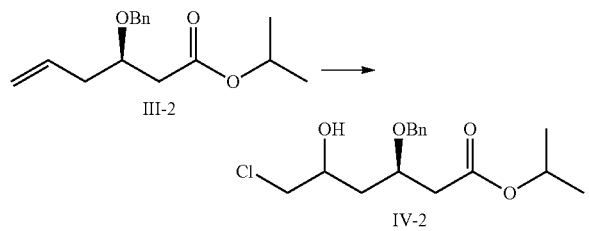

15 g of a compound represented by formula III-2 (GC: 86.5%) and 200 mL of acetone are added to a 1 L reaction flask, the temperature of the system is dropped to 0-15° C. after complete dissolution, 10 g of N-chlorosuccinimide is added in batches, then the system reacts with heat preservation at the temperature of 25-35° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 17.6 g of crude product of the compound represented by formula IV-2, its purity detected by GC (gas chromatography) is 87.1%, and its yield is 98.2%.

f. Preparation of a Compound Represented by Formula V-2

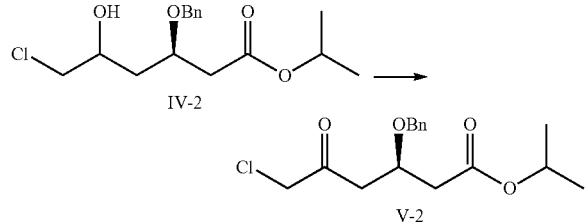

18 g of a compound represented by formula IV-2 (GC: 87.1%), 0.2 g of tetrabutylammonium bromide, 0.4 g of potassium bromide and 0.2 g of TEMPO are added to a 500 mL reaction flask, then 150 mL of n-hexane is added, 35 mL of sodium bicarbonate solution is added after the system is cooled to −10-10° C., 100 g of sodium hypochlorite is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 16.8 g light yellow liquid, i.e., the compound represented by formula V-2, its purity detected by GC (gas chromatography) is 72.2%, and its yield is 78.0%.

g. Preparation of a Compound Represented by Formula I-2

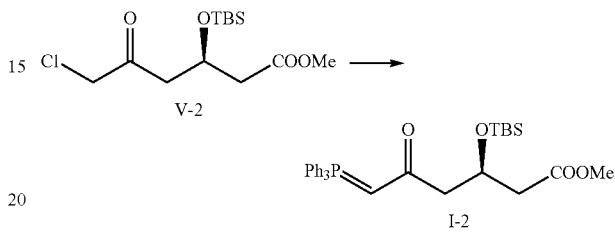

18 g of a compound represented by formula V-2 (GC: 72.2%), 26.0 g of triphenylphosphine, 18.2 g of potassium carbonate and 61.5 mL of methanol are added to the 500 mL reaction flask, and the system reacts at the temperature of −10° C.-10° C. In the middle control of GC, 100 mL of water is added to the system for dissolution of solid after complete reaction of the compound represented by formula V-2, extraction is carried out by three times with 100 mL×3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-2, 40 g of ethyl acetate/petroleum ether (2:1) is added for crystallization, 7.44 g of a compound represented by formula I-2 is obtained after filtering and drying, it purity detected by HPLC (high-performance liquid chromatography) is 97.1%, its ee value is 99.8%, and its yield is 32.3%.

MS: m/z=539.7 [M+H]+

Example 3

Preparation of a compound represented by formula I-3,

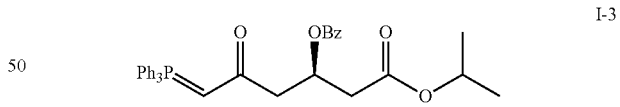

which is originated from formula I in which R is isopropyl, and Y is Bz.

The preparation steps a and b are the same as the steps a and b in example 1, and the step c is the same as step c in example 2.

d. Preparation of a Compound Represented by Formula III-3

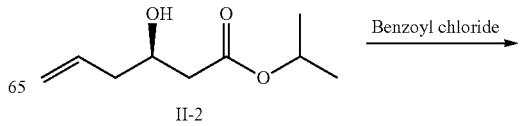

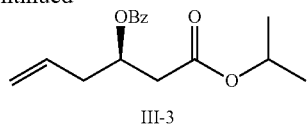

34 g of imidazole, 50 mL of methylene chloride, and 37 g of a compound represented by formula II-2 (HPLC: 93.1%) are added to the reaction flask for stirring to become clear, a mixed liquor of 39.0 g of benzoyl chloride and 70 mL of methylene chloride is dripped, then reaction is carried out during stirring at the temperature of 25-30° C., the reaction progress is monitored by thin-layer chromatography (The developing agent is a mixed liquor of petroleum ether-ethyl acetate (3:1 in volume ratio)) until the complete reaction of the compound represented by formula II-3, then the reaction liquid is transferred to 100 mL of water, extraction is carried out by three times with 150 g of methylene chloride, organic phases are combined, washing is carried out with 100 mL of saturated sodium bicarbonate solution and 100 mL of saturated sodium chloride solution, solvents are evaporated at the temperature of 30-35° C. and under the vacuum degree of 250-350 Pa to obtain 56.7 g of light yellow liquid, i.e., the compound represented by formula III-3, its purity detected by gas chromatography is 89.5%, and its yield is 91.7%.

e. Preparation of a Compound Represented by Formula IV-3

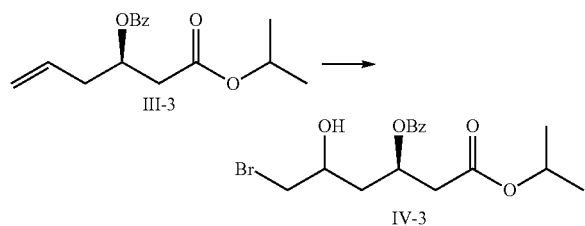

17.2 g of a compound represented by formula III-3 (GC: 89.5%) and 200 mL of acetone are added to a 1 L reaction flask, the temperature of the system is dropped to 0-15° C. after complete dissolution, 10 g of N-bromosuccinimide is added in batches, then the system reacts with heat preservation at the temperature of 30-40° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 23.2 g of crude product of the compound represented by formula IV-3, its purity detected by GC (gas chromatography) is 87.6%, and its yield is 97.6%.

f. Preparation of a Compound Represented by Formula V-3

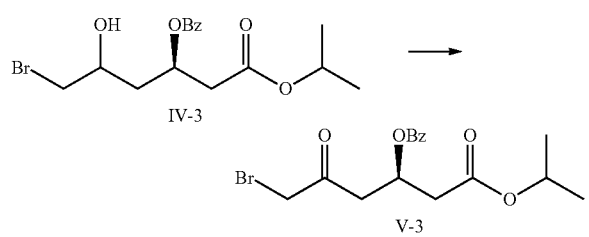

21.3 g of a compound represented by formula IV-3 (GC: 87.6%), 0.4 g of benzyltriethylammonium chloride, 0.3 g of TEMPO, and 0.4 g of potassium bromide are added to a 500 mL reaction flask, then 150 mL of n-hexane is added, 35 mL of sodium bicarbonate solution is added after the system is cooled to −10-10° C., 130 g of sodium hypochlorite is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 19.7 g light yellow liquid, i.e., the compound represented by formula V-3, its purity detected by GC (gas chromatography) is 72.8%, and its yield is 77.2%.

g. Preparation of a Compound Represented by Formula I-3

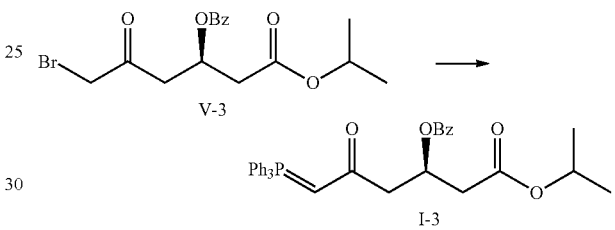

21.5 g of a compound represented by formula V-3 (GC: 72.8%), 26.0 g of triphenylphosphine, 18.2 g of potassium carbonate and 61.5 mL of DMF are added to the 500 mL reaction flask, and the system reacts at the temperature of −10-20° C. In the middle control of GC, 100 mL of water is added to the system for dissolution of solid after complete reaction of the compound represented by formula V-3, extraction is carried out by three times with 100 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-3, 60 g of ethyl acetate/petroleum ether (2:1) is added for crystallization, 7.5 g of a compound represented by formula I-3 is obtained after filtering and drying, its purity detected by HPLC (high-performance liquid chromatography) is 97.6%, its ee value is 99.8%, and its yield is 31.4%.

MS: m/z=553.5 [M+H]+

Example 4

Preparation of a compound represented by formula I-4

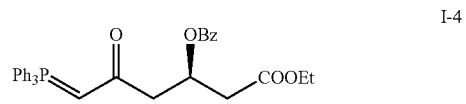

which is originated from formula I in which R is ethyl, and Y is Bz.

The preparation steps a and b are the same as the steps a and b in example 1.

c. Carrying out Alcoholysis Reaction Between the (2R)-1-cyano-2-hydroxyl-4-pentene and Ethanol Under the Action of Dried Hydrogen Chloride Gas to Obtain a Compound Represented by Formula II-3

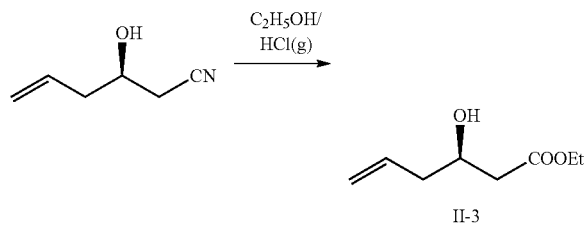

350 mL of absolute ethyl alcohol and 62 g of (2R)-1-cyano-2-hydroxyl-4-pentene (GC: 99.6%) are added to the reaction flask to be evenly stirred, dried hydrogen chloride gas is introduced for reaction by stirring at the room temperature, the reaction progress is monitored by thin-layer chromatography (The developing agent is a mixed liquor of petroleum ether-ethyl acetate (1:1 in volume ratio)) until the complete reaction of (2R)-1-cyano-2-hydroxyl-4-pentene, a part of ethanol in the reaction liquid is evaporated at the temperature of 35° C. and under the vacuum degree of 250-350 Pa, 400 mL of water is added for uniform mixing, extraction is carried out by three times with 600 g of chloroform, organic phases are combined, washing is carried out with 200 mL of saturated sodium bicarbonate solution, drying is carried out with 100 g of anhydrous sodium sulfate, solvents are evaporated at the temperature of 45° C. and under the vacuum degree of 250-350 Pa to obtain 68.7 g of brown liquid, i.e., the compound represented by formula II-3, its purity detected by HPLC (High-performance liquid chromatography) is 93.5%, and its yield is 73.1%.

d. Preparation of a Compound Represented by Formula III-4

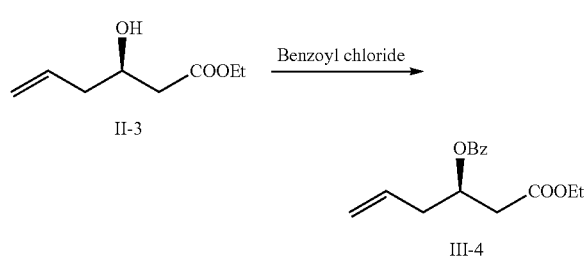

12.7 g of imidazole, 50 mL of methylene chloride, and 35 g of a compound represented by formula II-3 (HPLC: 93.5%) are added to the reaction flask for stirring to become clear, a mixed liquor of 39.0 g of benzoyl chloride and 70 mL of methylene chloride is dripped, then reaction is carried out during stirring at the temperature of 25-30° C., the reaction progress is monitored by thin-layer chromatography (The developing agent is a mixed liquor of petroleum ether-ethyl acetate (3:1 in volume ratio)) until the complete reaction of the compound represented by formula II-3, then the reaction liquid is transferred to 100 mL of water, extraction is carried out by three times with 150 g of methylene chloride, organic phases are combined, washing is carried out with 100 mL of saturated sodium bicarbonate solution and 100 mL of saturated sodium chloride solution, solvents are evaporated at the temperature of 30-35° C. and under the vacuum degree of 250-350 Pa to obtain 55.3 g of light yellow liquid, i.e., the compound represented by formula III-4, its purity detected by gas chromatography is 89.9%, and its yield is 91.6%.

e. Preparation of a Compound Represented by Formula IV-4

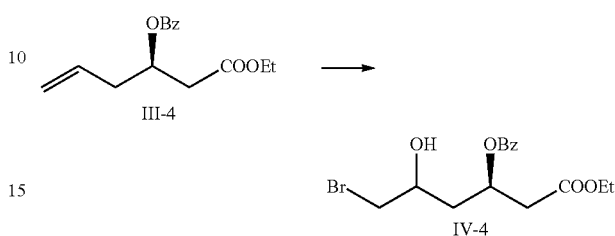

16 g of a compound represented by formula III-4 (GC: 89.9%) and 200 mL of acetone are added to a 1 L reaction flask, the temperature of the system is dropped to 0-10° C. after complete dissolution, 9 g of N-chlorosuccinimide is added in batches, then the system reacts with heat preservation at the temperature of 20-30° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 22.0 g of crude product of the compound represented by formula IV-4, its purity detected by GC (gas chromatography) is 88.1%, and its yield is 98.2%.

f. Preparation of a Compound Represented by Formula V-4

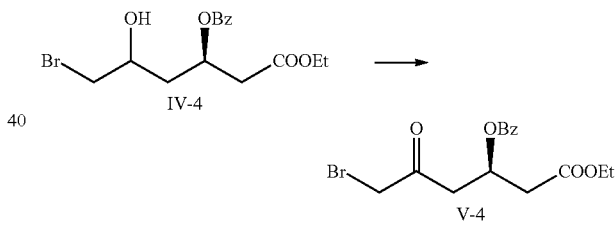

20 g of a compound represented by formula IV-4 (GC: 88.1%), 0.3 g of tetrabutyl ammonium hydrogen sulfate and 0.4 g of potassium bromide are added to a 500 mL reaction flask, then 150 mL of n-hexane is added, 35 mL of sodium bicarbonate solution is added after the system is cooled to −10-10° C., 115 g of sodium hypochlorite is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 18.6 g light yellow liquid, i.e., the compound represented by formula V-4, its purity detected by GC (gas chromatography) is 72.4%, and its yield is 77.0%.

g. Preparation of a Compound Represented by Formula I-4

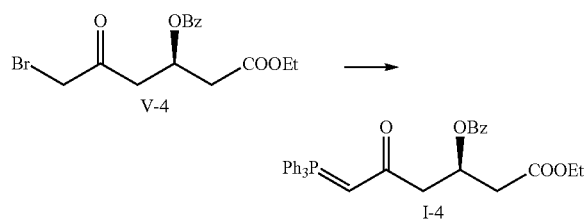

21 g of a compound represented by formula IV-4 (GC: 72.4%), 26.0 g of triphenylphosphine, 18.2 g of potassium carbonate and 61.5 mL of methylene chloride are added to the 500 mL reaction flask, and the system reacts at the temperature of 15-30° C. In the middle control of GC, 100 mL of water is added to the system for dissolution of solid after complete reaction of the compound represented by formula IV-4, extraction is carried out by three times with 100 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-4, 60 g of ethyl acetate/petroleum ether (2:1) is added for crystallization, 7.2 g of a compound represented by formula I-4 is obtained after filtering and drying, it purity detected by HPLC (high-performance liquid chromatography) is 97.5%, its ee value is 99.8%, and its yield is 30.7%.

MS: m/z=539.4 [M+H]+

Example 5

Preparation of a Compound Represented by Formula I-1

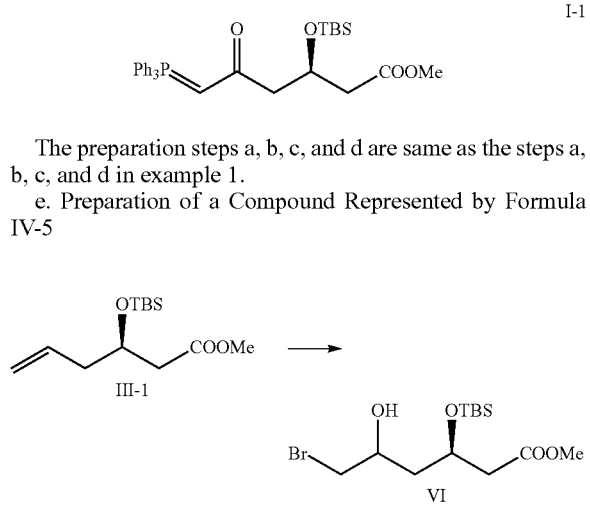

The preparation steps a, b, c, and d are same as the steps a, b, c, and d in example 1.

e. Preparation of a Compound Represented by Formula IV-5

22.1 g of a compound represented by formula III-1 (GC: 90.5%) and 280 mL of acetone are added to a reaction flask, the temperature of the system is dropped to 0-15° C. after complete dissolution, 20.6 g of N-bromosuccinimide is added in batches, then the system reacts with heat preservation at the temperature of −10-0° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 30.1 g of crude product of the compound represented by formula IV-5, its purity detected by GC (gas chromatography) is 86.8%, and its yield is 95.4%.

1H NMR (300 MHz, CDCl$_3$): δ4.31-4.35 (m, 1H), δ3.95-4.05 (m, 1H), δ3.66 (s, 3H), 3.36-3.46 (m, 2H), δ3.22 and 2.95 (2×d, 1H), δ2.54-2.59 (m, 2H), δ1.75-1.81 (m, 2H), δ0.86, (s, 9H), δ0.09 (m, 6H).

f. Preparation of a Compound Represented by Formula V-5

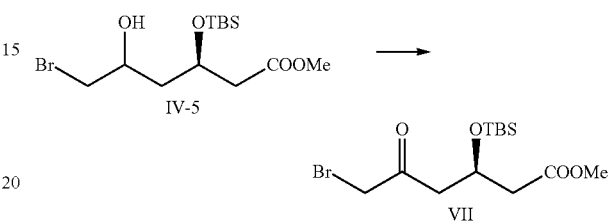

34.6 g of a compound represented by formula IV-5 (GC: 86.8%), 0.3 g of methyltrioctylammonium chloride, 0.4 g of TEMPO and 0.5 g of potassium bromide are added to a 500 mL reaction flask, then 250 mL of methylene chloride is added, 57 mL of sodium bicarbonate solution is added after the system is cooled to −10-10° C., 100 g of sodium hypochlorite is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 28.5 g light yellow liquid, i.e., the compound represented by formula V-5, its purity detected by GC (gas chromatography) is 75.0%, and its yield is 72.1%.

1H NMR (600 MHz, CDCl$_3$): δ4.50-4.53 (m, 1H), δ3.87 (s, 2H), δ3.62 (s, 3H), δ2.80-2.89 (m, 2H), δ2.43-2.51 (m, 2H), δ0.79 (s, 9H), δ0.017 (d, J=5.5, 6H)

$[\alpha]_{D20}$=−4.6 (c=1.0, C$_2$H$_5$OH).

g. Preparation of a Compound Represented by Formula I-1

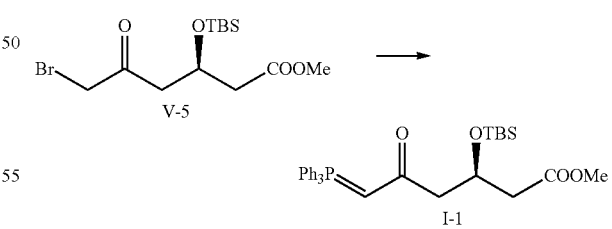

30 g of a compound represented by formula V-5 (GC: 75.0%), 26.9 g of triphenylphosphine, 18.6 g of potassium carbonate and 75 mL of methylene chloride are added to the 500 mL reaction flask, and the system reacts at the temperature of −10-10° C. In the middle control of GC, 150 mL of water is added to the system for dissolution of solid after complete reaction of the compound represented by formula V-5, extraction is carried out by three times with 150 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-1, 50 g of ethyl acetate/petroleum ether (2:1) is added for crystallization, 9.0 g of a compound represented by formula I-1 is obtained after filtering and drying, it purity detected by HPLC (high-performance liquid chromatography) is 98.2%, its ee value is 97.9%, and its yield is 25.4%.

1H NMR (300 MHz, CDCl$_3$): δ7.46-7.70 (m, 15H), δ4.54-4.59 (m, 1H), δ3.67 (s, 3H), δ2.73-2.77 (m, 1H), δ2.59-2.63 (m, 1H), δ2.45-2.55 (m, 2H), δ0.83 (s, 9H), δ0.03-0.06 (m, 6H).

MS: m/z=535.5 [M+H]+

Example 6

Preparation of a compound represented by formula I-1,

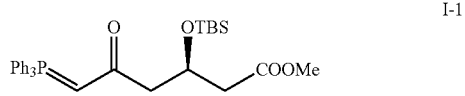
I-1 which is originated from formula I in which R is methyl, and Y is TBS.

The preparation steps a, b, c, and d are the same as the steps a, b, c, and d in example 1.

e. Preparation of a Compound Represented by Formula IV-6

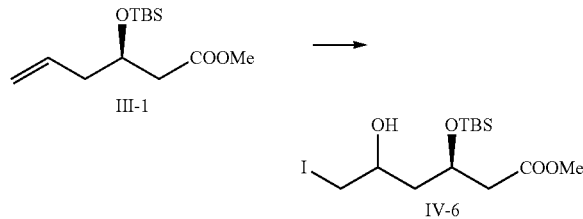

15.6 g of a compound represented by formula III-1 (GC: 89.6%) and 220 mL of acetone are added to a reaction flask, the temperature of the system is dropped to 0-15° C. after complete dissolution, 14.0 g of N-iodosuccinimide is added in batches, then the system reacts with heat preservation at the temperature of −5-5° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 22.6 g of crude product of the compound represented by formula IV-6, its purity detected by GC (gas chromatography) is 87.2%, and its yield is 90.9%.

f. Preparation of a Compound Represented by Formula V-6

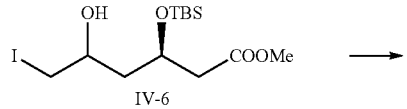

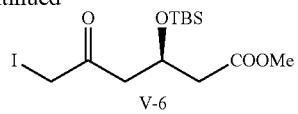
V-6

22.9 g of a compound represented by formula IV-6 (GC: 87.2%), 0.2 g of tetrabutylammonium bromide, 0.35 g of TEMPO and 0.3 g of potassium bromide are added to a 500 mL reaction flask, then 160 mL of methylene chloride is added, 38 mL of sodium bicarbonate solution is added after the system is cooled to −10-10° C., 110 g of sodium hypochlorite is slowly dripped during stirring, temperature is kept at −20-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 20.7 g light yellow liquid, i.e., the compound represented by formula V-6, its purity detected by GC (gas chromatography) is 72.7%, and its yield is 75.6%.

1H NMR (300 MHz, CDCl$_3$): δ4.50-4.58 (m, 1H), δ3.82 (s, 2H), δ3.65 (s, 3H), δ2.92-2.95 (m, 2H), δ2.43-2.57 (m, 2H), δ0.82 (s, 9H), δ0.038-0.075 (m, 6H).

g. Preparation of a Compound Represented by Formula I-1

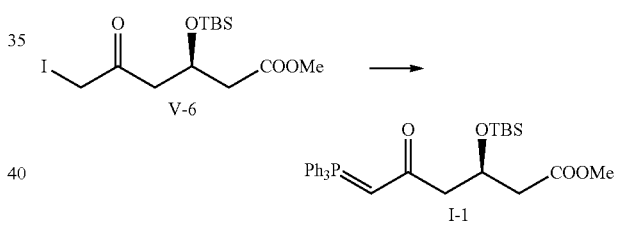

20.6 g of a compound represented by formula V-6 (GC: 72.7%), 15.7 g of triphenylphosphine, 10.4 g of potassium carbonate and 50 mL of methylene chloride are added to the 500 mL reaction flask, and the system reacts at the temperature of 10-27° C. In the middle control of GC, 100 mL of water is added to the system for dissolution of solid after complete reaction of the compound represented by formula V-6, extraction is carried out by three times with 100 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-1, 60 g of ethyl acetate/petroleum ether (2:1) is added for crystallization, 5.0 g of a compound represented by formula I-1 is obtained after filtering and drying, its purity detected by HPLC (high-performance liquid chromatography) is 97.4%, its ee value is 96.8%, and its yield is 23.7%.

1H NMR (300 MHz, CDCl$_3$): δ7.46-7.70 (m, 15H), δ4.54-4.59 (m, 1H), δ3.67 (s, 3H), δ2.73-2.77 (m, 1H), δ2.59-2.63 (m, 1H), δ2.45-2.55 (m, 2H), δ0.83 (s, 9H), δ0.03-0.06 (m, 6H).

MS: m/z=535.5 [M+H]+

Example 7

Preparation of a compound represented by formula I-1,

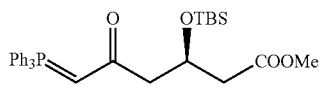

which is originated from formula I in which R is methyl, and Y is TBS.

The preparation steps a, b, c, and d are the same as the steps a, b, c, and d in example 1.

e. Preparation of a Compound Represented by Formula IV-6

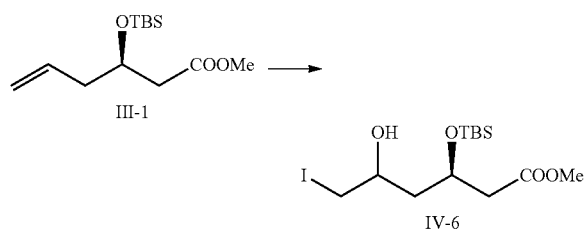

18.3 g of a compound represented by formula III-1 (GC: 87.4%) and 250 mL of acetone are added to a 1 L reaction flask, the temperature of the system is dropped to 0-15° C. after complete dissolution, 16.0 g of N-iodosuccinimide is added in batches, then the system reacts with heat preservation at the temperature of 15-25° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 26.1 g of crude product of the compound represented by formula IV-6, its purity detected by GC (gas chromatography) is 88.4%, and its yield is 92.6%.

f. Preparation of a Compound Represented by Formula V-6

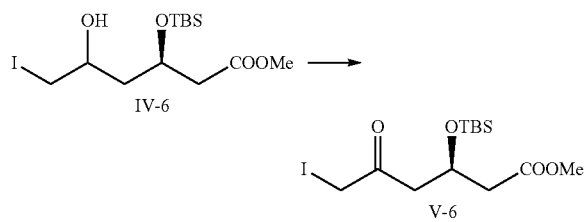

19.2 g of a compound represented by formula IV-6 (GC: 88.4%), 0.14 g of tetrabutylammonium chloride, 0.4 g of TEMPO and 0.25 g of potassium bromide are added to a 500 mL reaction flask, then 160 mL of methylene chloride is added, 38 mL of sodium bicarbonate solution is added after the system is cooled to −10-10° C., 120 g of NaClO$_2$ is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 17.5 g light yellow liquid, i.e., the compound represented by formula V-6, its purity detected by GC (gas chromatography) is 73.2%, and its yield is 76.4%.

1H NMR (300 MHz, CDCl$_3$): δ4.50-4.58 (m, 1H), δ3.82 (s, 2H), δ3.65 (s, 3H), δ2.92-2.95 (m, 2H), 62.43-2.57 (m, 2H), 60.82 (s, 9H), δ0.038-0.075 (m, 6H).

g. Preparation of a Compound Represented by Formula I-1

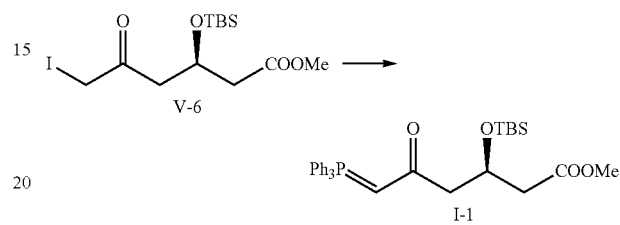

16.6 g of a compound represented by formula V-6 (GC: 73.2%), 12.8 g of triphenylphosphine, 8.4 g of potassium carbonate and 57.5 mL of methylene chloride are added to the 500 mL reaction flask, and the system reacts at the temperature of −10-10° C. In the middle control of GC, 95 mL of water is added to the system for dissolution of solid after complete reaction of the compound represented by formula V-6, extraction is carried out by three times with 95 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-1, 50 g of ethyl acetate/petroleum ether (2:1) is added for crystallization, 4.9 g of a compound represented by formula I-1 is obtained after filtering and drying, it purity detected by HPLC (high-performance liquid chromatography) is 97.6%, its ee value is 98.5%, and its yield is 28.7%.

1H NMR (300 MHz, CDCl$_3$): δ7.46-7.70 (m, 15H), δ4.54-4.59 (m, 1H), δ3.67 (s, 3H), δ2.73-2.77 (m, 1H), δ2.59-2.63 (m, 1H), δ2.45-2.55 (m, 2H), δ0.83 (s, 9H), 60.03-0.06 (m, 6H).

MS: m/z=535.5 [M+H]+

Example 8

Preparation of a compound represented by formula I-4,

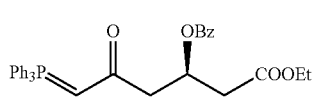

which is originated from formula I in which R is ethyl, and Y is Bz.

The preparation steps a and b are the same as the steps a and b in example 1.

c. Carrying Out Alcoholysis Reaction Between the (2R)-1-cyano-2-hydroxyl-4-pentene and Ethanol Under the Action of Concentrated Sulphuric Acid to Obtain a Compound Represented by Formula II-3

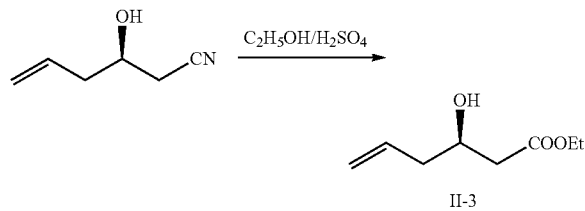

II-3

250 mL of absolute ethyl alcohol and 45.0 g of (2R)-1-cyano-2-hydroxyl-4-pentene (GC: 98.7%) are added to the reaction flask to be evenly stirred, 60.0 g of concentrated sulphuric acid is added for reaction by stirring at the room temperature, the reaction progress is monitored by thin-layer chromatography (The developing agent is a mixed liquor of petroleum ether-ethyl acetate (1:1 in volume ratio)) until the complete reaction of (2R)-1-cyano-2-hydroxyl-4-pentene, a part of ethanol in the reaction liquid is evaporated at the temperature of 35° C. and under the vacuum degree of 250-350 Pa, 285 mL of water is added for uniform mixing, extraction is carried out by three times with 430 g of chloroform, organic phases are combined, washing is carried out with 145 mL of saturated sodium bicarbonate solution, drying is carried out with 70 g of anhydrous sodium sulfate, solvents are evaporated at the temperature of 45° C. to obtain 54.2 g of brown liquid, i.e., the compound represented by formula II-3, its purity detected by HPLC (High-performance liquid chromatography) is 93.2%, and its yield is 79.5%.

d. Preparation of a Compound Represented by Formula III-4

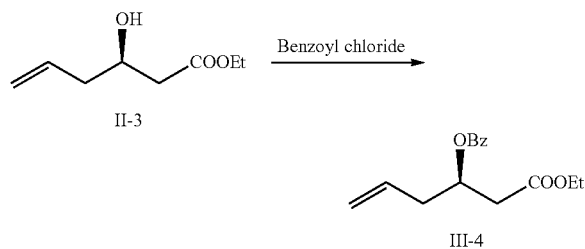

33.0 g of imidazole, 50 mL of ethyl acetate and 35.8 g of a compound represented by formula II-3 (HPLC: 93.2%) are added to the reaction flask for stirring to become clear, a mixed liquor of 37.9 g of benzoyl chloride and 70 mL of methylene chloride is dripped, then reaction is carried out during stirring at the temperature of 25-30° C., the reaction progress is monitored by thin-layer chromatography (The developing agent is a mixed liquor of petroleum ether-ethyl acetate (3:1 in volume ratio)) until the complete reaction of the compound represented by formula II-3, then the reaction liquid is transferred to 100 mL of water, extraction is carried out by three times with 150 g of methylene chloride, organic phases are combined, washing is carried out with 100 mL of saturated sodium bicarbonate solution and 100 mL of saturated sodium chloride solution, solvents are evaporated at the temperature of 30-35° C. and under the vacuum degree of 250-350 Pa to obtain 56.4 g of light yellow liquid, i.e., the compound represented by formula III-4, its purity detected by gas chromatography is 90.6%, and its yield is 93.2%.

e. Preparation of a Compound Represented by Formula IV-4

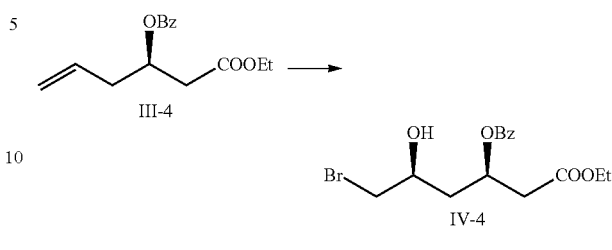

16.0 g of a compound represented by formula III-4 (GC: 90.6%) and 200 mL of acetone are added to a reaction flask, the temperature of the system is dropped to 0-15° C. after complete dissolution, 11.3 g of N-bromosuccinimide is added in batches, then the system reacts with heat preservation at the temperature of 0-10° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 21.4 g of crude product of the compound represented by formula IV-4, its purity detected by GC (gas chromatography) is 86.9%, and its yield is 93.5%.

f. Preparation of a Compound Represented by Formula V-4

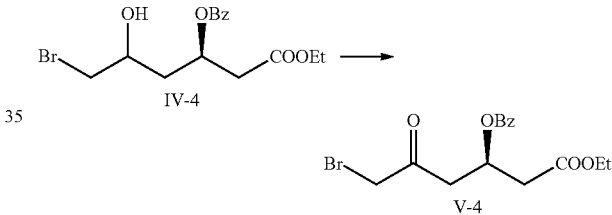

20.5 g of a compound represented by formula IV-4 (GC: 86.9%), 0.16 g of tetrabutylammonium bromide, 0.5 g of TEMPO and 0.29 g of potassium bromide are added to a 500 mL reaction flask, then 150 mL of methylene chloride is added, 33.4 mL of sodium bicarbonate solution is added after the system is cooled to −10-10° C., 110 g of NaClO2 is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 19.0 g light yellow liquid, i.e., the compound represented by formula V-4, its purity detected by GC (gas chromatography) is 72.6%, and its yield is 78.0%.

g. Preparation of a Compound Represented by Formula I-4

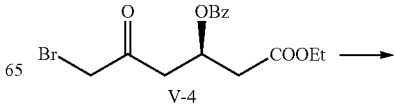

-continued

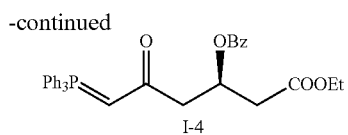

17.9 g of a compound represented by formula V-4 (GC: 72.6%), 15.3 g of triphenylphosphine, 10.1 g of potassium carbonate and 50 mL of DMF are added to the 500 mL reaction flask, and the system reacts at the temperature of 35-50° C. In the middle control of GC, 85 mL of water is added to the system for dissolution of solid after complete reaction of the compound represented by formula V-4, extraction is carried out by three times with 85 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-4, 55 g of ethyl acetate/petroleum ether (2:1) is added for crystallization, 6.2 g of a compound represented by formula I-4 is obtained after filtering and drying, it purity detected by HPLC (high-performance liquid chromatography) is 97.8%, its ee value is 98.2%, and its yield is 30.4%.

MS: m/z=539.4 [M+H]+

Example 9

Preparation of a compound represented by formula I-5,

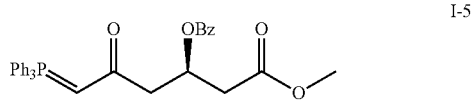

which is originated from formula I in which R is Me, and Y is Bz.

The preparation steps a, b, and c are the same as the steps a, b, and c in example 1.

d. Preparation of a Compound Represented by Formula III-1

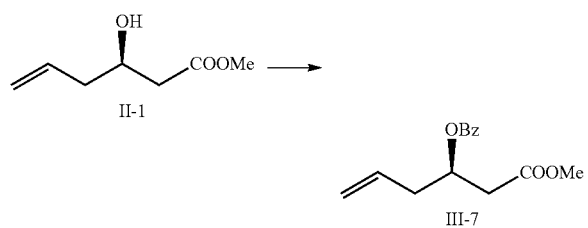

55.3 g of imidazole, 80 mL of acetone and 58.0 g of a compound represented by formula II-1 (HPLC: 91.8%) are added to the reaction flask for stirring to become clear, a mixed liquor of 60.2 g of benzoyl chloride and 110 mL of methylene chloride is dripped, then reaction is carried out during stirring at the temperature of 25-30° C., the reaction progress is monitored by thin-layer chromatography (The developing agent is a mixed liquor of petroleum ether-ethyl acetate (3:1 in volume ratio)) until the complete reaction of the compound represented by formula II-1, then the reaction liquid is transferred to 155 mL of water, extraction is carried out by three times with 240 g of methylene chloride, organic phases are combined, washing is carried out with 155 mL of saturated sodium bicarbonate solution and 155 mL of saturated sodium chloride solution, solvents are evaporated at the temperature of 30-35° C. and under the vacuum degree of 250-350 Pa to obtain 97.0 g of light yellow liquid, i.e., the compound represented by formula III-1, its purity detected by gas chromatography is 90.7%, and its yield is 92.2%.

e. Preparation of a Compound Represented by Formula IV-7

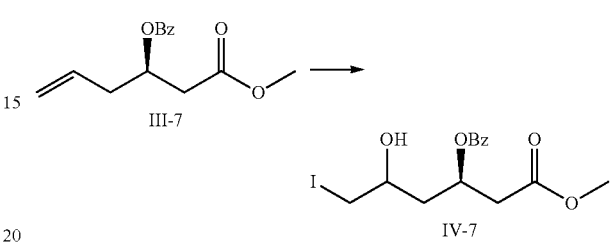

19.5 g of a compound represented by formula III-1 (GC: 90.7%) and 230 mL of n-hexane are added to a reaction flask, the temperature of the system is dropped to 0-15° C. after complete dissolution, 18.4 g of N-iodosuccinimide is added in batches, then the system reacts with heat preservation at the temperature of 10-20° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 30.2 g of crude product of the compound represented by formula IV-7, its purity detected by GC (gas chromatography) is 89.3%, and its yield is 96.4%.

f. Preparation of a Compound Represented by Formula V-7

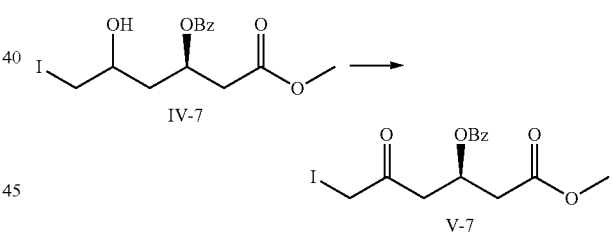

22.0 g of a compound represented by formula IV-7 (GC: 89.4%), 0.16 g of tetrabutylammonium bromide, 0.4 g of TEMPO and 0.30 g of potassium bromide are added to a 500 mL reaction flask, then 160 mL of n-hexane is added, 37 mL of sodium bicarbonate solution is added after the system is cooled to −10-10° C., 100 g of NaClO2 is slowly dripped during stirring, temperature is kept at 10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 19.1 g light yellow liquid, i.e., the compound represented by formula V-7, its purity detected by GC (gas chromatography) is 77.4%, and its yield is 75.9%.

g. Preparation of a Compound Represented by Formula I-5

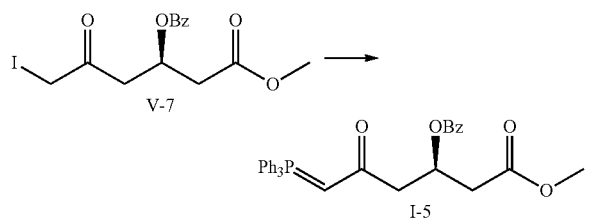

18.6 g of a compound represented by formula V-7 (GC: 77.4%), 15.5 g of triphenylphosphine, 10.2 g of potassium carbonate and 56.6 mL of n-hexane are added to the 500 mL reaction flask, and the system reacts at the temperature of 30-45° C. In the middle control of GC, 95 mL of water is added to the system for dissolution of solid after complete reaction of the compound represented by formula V-7, extraction is carried out by three times with 95 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-5, 50 g of ethyl acetate/petroleum ether (2:1) is added for crystallization, 5.9 g of a compound represented by formula I-5 is obtained after filtering and drying, it purity detected by HPLC (high-performance liquid chromatography) is 98.3%, its ee value is 98.8%, and its yield is 29.5%.

MS: m/z=524.1 [M+H]+

Example 10

Preparation of a compound represented by formula I-6,

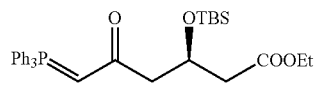

which is originated from formula I in which R is ethyl, and Y is TBS.

The preparation steps a and b are the same as the steps a and b in example 1, and the step c is the same as step c in example 4.

d. Preparation of a Compound Represented by Formula III-4

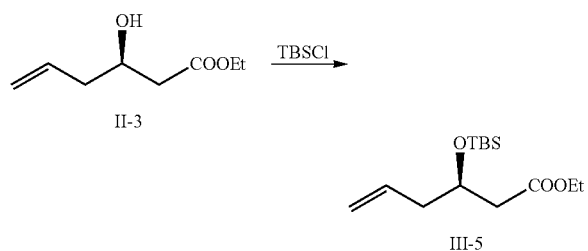

42.3 g of imidazole, 65 mL of ethyl acetate and 45.5 g of a compound represented by formula II-3 (HPLC: 94.1%, and the mol ratio between the imidazole and the compound represented by formula II-3 is 2.3:1) are added to the reaction flask for stirring to become clear, a mixed liquor of 59.0 g of tert-butyldimethylsilyl chloride and 90 mL of methylene chloride is dripped, then reaction is carried out during stirring at the temperature of 25-30° C., the reaction progress is monitored by thin-layer chromatography (The developing agent is a mixed liquor of petroleum ether-ethyl acetate (3:1 in volume ratio)) until the complete reaction of the compound represented by formula II-3, then the reaction liquid is transferred to 130 mL of water, extraction is carried out by three times with 190 g of methylene chloride, organic phases are combined, washing is carried out with 130 mL of saturated sodium bicarbonate solution and 130 mL of saturated sodium chloride solution, solvents are evaporated at the temperature of 30-35° C. and under the vacuum degree of 250-350 Pa to obtain 75.5 g of light yellow liquid, i.e., the compound represented by formula III-5, its purity detected by gas chromatography is 89.6%, and its yield is 91.7%.

e. Preparation of a Compound Represented by Formula IV-8

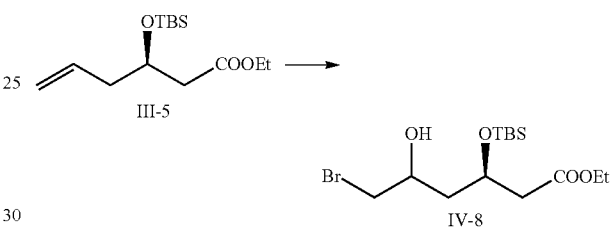

13.4 g of a compound represented by formula III-5 (GC: 89.6%) and 195 mL of acetone are added to a 1 L reaction flask, the temperature of the system is dropped to 0-15° C. after complete dissolution, 9.0 g of N-bromosuccinimide is added in batches, then the system reacts with heat preservation at the temperature of 25-35° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 17.7 g of crude product of the compound represented by formula IV-8, its purity detected by GC (gas chromatography) is 88.4%, and its yield is 96.2%.

f. Preparation of a Compound Represented by Formula V-8

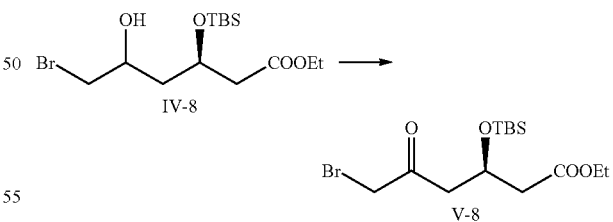

17.6 g of a compound represented by formula IV-8 (GC: 88.4%), 0.14 g of tetrabutylammonium bromide, 0.4 g of TEMPO and 0.25 g of potassium bromide are added to a 500 mL reaction flask, then 130 mL of DMF is added, 30 mL of sodium bicarbonate solution is added after the system is cooled to −10-10° C., 110 g of NaClO2 is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 17.1 g light yellow liquid, i.e., the compound represented by formula V-8, its purity detected by GC (gas chromatography) is 71.8%, and its yield is 79.5%.

g. Preparation of a Compound Represented by Formula I-6

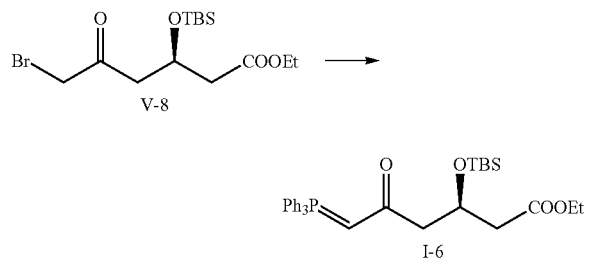

16.7 g of a compound represented by formula V-8 (GC: 71.8%), 13.7 g of triphenylphosphine, 9.0 g of potassium carbonate and 45 mL of chloroform are added to the 500 mL reaction flask, and the system reacts at the temperature of −10-10° C. In the middle control of GC, 85 mL of water is added to the system for dissolution of solid after complete reaction of the compound represented by formula V-8, extraction is carried out by three times with 85 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-6, 55 g of ethyl acetate/petroleum ether (2:1) is added for crystallization, 5.0 g of a compound represented by formula I-6 is obtained after filtering and drying, it purity detected by HPLC (high-performance liquid chromatography) is 98.3%, its ee value is 96.7%, and its yield is 26.4%.

1H NMR (300 MHz, CDCl$_3$): δ7.45-7.69 (m, 15H), δ4.52-4.59 (m, 1H), δ4.11-4.14 (m, 2H), δ2.70-2.76 (m, 1H), δ2.60-2.63 (m, 1H), δ2.45-2.55 (m, 2H), δ1.20 (t, 3H), δ0.84 (s, 9H), δ0.03-0.07 (m, 6H).

MS: m/z=549.3 [M+H]+

Example 11

Preparation of a compound represented by formula I-4,

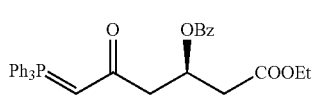

which is originated from formula I in which R is ethyl, and Y is Bz.

The preparation steps a and b are the same as the steps a and b in example 1, and the steps c and d are the same as step c and d in example 4.

e. Preparation of a Compound Represented by Formula IV-9

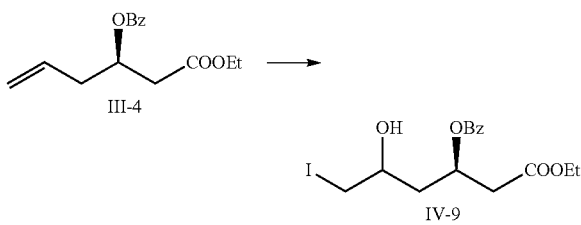

18.9 g of a compound represented by formula III-4 (GC: 90.1%) and 280 mL of acetone are added to a reaction flask, the temperature of the system is dropped to 0-15° C. after complete dissolution, 16.8 g of N-iodosuccinimide is added in batches, then the system reacts with heat preservation at the temperature of 15-25° C., and sampling is tracked until the completion of reaction (The vanishing raw material is monitored by TLC (thin-layer chromatography)). Solvents are evaporated at the temperature of 30-35° C. and under the vacuum degree of 250-350 Pa to obtain a light yellow liquid, i.e., 28.9 g of crude product of the compound represented by formula IV-9, its purity detected by GC (gas chromatography) is 87.3%, and its yield is 95.8%.

f. Preparation of a Compound Represented by Formula V-9

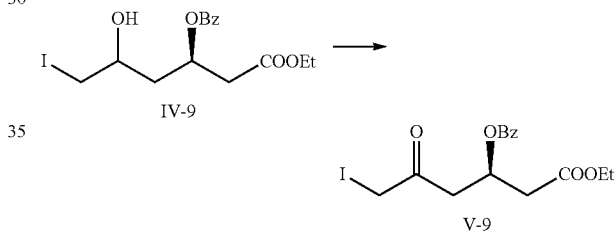

21.8 g of a compound represented by formula IV-9 (GC: 87.3%), 0.15 g of tetrabutylammonium bromide, 0.4 g of TEMPO, 0.28 g of potassium bromide and 0.07 g of NaClO2 are added to a 500 mL reaction flask, then 155 mL of methylene chloride is added, 36.5 mL of sodium bicarbonate solution (3%) is added after the system is cooled to −10-10° C., 10 g of hydrogen peroxide is slowly dripped during stirring, temperature is kept at −10-20° C. during dripping, and after the completion of dripping, the system reacts with heat preservation at the temperature of −10-10° C. After the complete reaction, saturated sodium thiosulfate is added for quenching the reaction, an aqueous phase is separated out after water is added for washing, organic phases are washed with a proper amount of water and saturated salt solution, dried with anhydrous sodium sulfate, filtered and then concentrated at the temperature of 30-35° C. and under the vacuum degree of 250-350 Pa to obtain 19.6 g light yellow liquid, i.e., the compound represented by formula V-9, its purity detected by GC (gas chromatography) is 73.9%, and its yield is 76.4%.

g. Preparation of a Compound Represented by Formula I-4

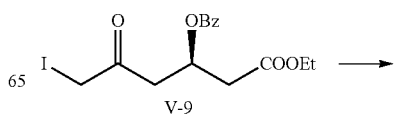

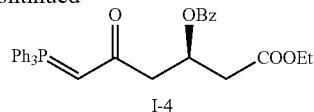

I-4

18.5 g of a compound represented by formula V-9 (GC: 73.9%), 14.2 g of triphenylphosphine, 9.3 g of potassium carbonate and 60 mL of acetonitrile are added to the 500 mL reaction flask, and the system reacts at the temperature of 30-45° C. In the middle control of GC, 95 mL of water is added to the system for dissolution of solid after complete reaction of the compound represented by formula V-9, extraction is carried out by three times with 95 mL*3 of methyl tert-butyl ether, organic phases are filtered after being dried with anhydrous sodium sulfate, and then concentrated at the temperature of 30-35° C. and under the vacuum degree of 250-350 Pa to obtain an oily substance, i.e., the compound represented by formula I-4, 50 g of ethyl acetate/petroleum ether (2:1) is added for crystallization, 4.5 g of a compound represented by formula I-4 is obtained after filtering and drying, it purity detected by HPLC (high-performance liquid chromatography) is 97.4%, its ee value is 95.8%, and its yield is 23.2%.

MS: m/z=539.4 [M+H]+

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing a compound represented by formula I,

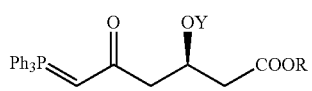

I the method comprising:
a) reacting monohalogenated ethene with magnesium to obtain a Grignard reagent;
b) carrying out a Grignard reaction between the Grignard reagent and R-epichlorohydrin in the presence of a catalyst selected from the group consisting of cuprous chloride, cuprous iodide, and cuprous cyanide to obtain (2R)-1-halogeno-2-hydroxyl-4-pentene;
c) carrying out a nucleophilic substitution reaction between the (2R)-1-halogeno-2-hydroxyl-4-pentene and sodium cyanide to obtain (2R)-1-cyano-2-hydroxyl-4-pentene;
d) carrying out an alcoholysis reaction between the (2R)-1-cyano-2-hydroxyl-4-pentene and an alcohol in the presence of dried hydrogen chloride gas or concentrated sulphuric acid to obtain a compound represented by formula II;

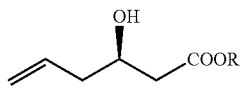

II e) performing a hydroxyl protection to the compound represented by formula II in a mixture of imidazole and an organic solvent selected from the group consisting of methylene chloride, ethyl acetate, and acetone to obtain a compound represented by formula III;

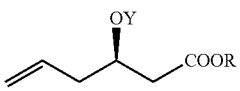

III f) reacting the compound represented by formula III with a reagent selected from the group consisting of N-chlorosuccinimide, N-bromosuccinimide, and N-iodosuccinimide in a solvent B to obtain a compound represented by formula IV, wherein the solvent B is selected from the group consisting of methylene chloride, chloroform, carbon tetrachloride, ethyl acetate, butyl acetate, toluene, benzol, acetonitrile, acetone, butanone, methanol, ethanol, isopropyl alcohol, n-hexane, cyclohexane, n-heptane, DMF, DMA, DMSO, a mixture thereof, and an aqueous solution thereof;

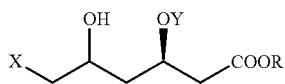

IV g) in the presence of 2,2,6,6-tetramethylpiperidine-N-oxide, an oxidant, and a phase-transfer catalyst, oxidizing a hydroxyl of the compound represented by formula IV in a solvent A to obtain a compound represented by formula V,
wherein the solvent A is selected from the group consisting of methylene chloride, chloroform, carbon tetrachloride, ethyl acetate, butyl acetate, toluene, benzol, acetonitrile, acetone, butanone, n-hexane, cyclohexane, n-heptane, DMF, DMA, DMSO, a mixture thereof, and an aqueous solution thereof; and

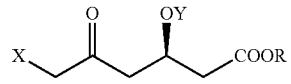

V h) contacting the compound represented by formula V with triphenylphosphine under alkaline conditions to obtain the compound represented by formula I;
wherein
R represents alkyl, Y represents a hydroxyl protecting group, and X represents a halogen atom.

2. The method of claim 1, wherein R represents C1-C3 alkyl, Y represents tert-butyldimethylsilyl, benzyl, or benzoyl, and X is chlorine, bromine, or iodine.

3. The method of claim 1, wherein the alkaline conditions are provided by adding an alkali metal oxide, an alkaline-earth metal oxide, a hydroxide, a carbonate, a bicarbonate, or a mixture thereof to a reaction liquid.

4. The method of claim 1, wherein
   the oxidant is sodium hypochlorite or sodium chlorite; and
   the phase-transfer catalyst is benzyltriethylammonium chloride, tetrabutyl ammonium bromide, tetrabutylammonium chloride, tetrabutyl ammonium hydrogen sulfate, methyltrioctylammonium chloride, or hexadecyltrimethylammonium chloride.

5. The method of claim 1, wherein step f) is performed at a temperature of between −10 and 50° C.

6. The method of claim 1, wherein in step b), a mol ratio between the catalyst and R-epichlorohydrin is 0.10-0.15:1.

7. The method of claim 1, wherein in step e), a mol ratio between the imidazole and the compound represented by formula II is 1.5-2.5:1.

8. The method of claim 1, wherein the compound represented by formula I is obtained in a purity of above 96.5% and an enantiomeric excess value of above 95.8%.

\* \* \* \* \*